(12) United States Patent
Silva

(10) Patent No.: US 6,858,734 B2
(45) Date of Patent: Feb. 22, 2005

(54) PREPARATION OF (S)-CLOPIDOGREL AND RELATED COMPOUNDS

(75) Inventor: Richard A. Silva, Foxborough, MA (US)

(73) Assignee: Rhodia Pharma Solutions Inc., Cranbury, NJ (US)

( * ) Notice: Subject to any disclaimer, the term of this patent is extended or adjusted under 35 U.S.C. 154(b) by 7 days.

(21) Appl. No.: 10/421,564

(22) Filed: Apr. 23, 2003

(65) Prior Publication Data

US 2004/0214878 A1 Oct. 28, 2004

(51) Int. Cl.$^7$ .................... C07D 515/02; C07D 401/02; C07D 409/02
(52) U.S. Cl. ........................................ 546/114; 514/301
(58) Field of Search ........................... 546/114; 514/301

(56) References Cited

U.S. PATENT DOCUMENTS 4,847,265 A  7/1989  Badorc et al. ............... 514/301

FOREIGN PATENT DOCUMENTS

| EP | 313472 | * | 4/1989 |
| FR | 2 530 247 | | 7/1982 |
| FR | 2 769 313 | | 10/1997 |

OTHER PUBLICATIONS

Vachal et al. "Enantioselective catalytic addition of HCN to ketoimines. Catalytic synthesis of quaternary amono acids." Org. Lett., vol. 2, No. 6, 2000, pp. 867–870 & S–1–S–32 (Supporting Information).

* cited by examiner

Primary Examiner—Rita Desai
(74) Attorney, Agent, or Firm—Ohlandt, Greeley, Ruggiero & Perle, LLP

(57) ABSTRACT

A process for producing enantiomerically enriched (S)-α-(2-chlorophenyl)-6,7-dihydrothieno[3,2-c]pyridine-5 (4H)-acetic acid hydrocarbyl ester, represented by the formula:

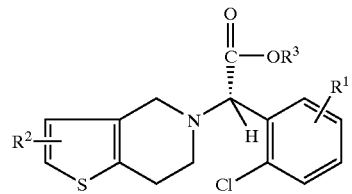

Is provided, wherein $R^1$ and $R^2$ are hydrogens and $R^3$ is methyl (i.e., (S)-Clopidogrel). The process includes the steps of: (a) contacting N-2-chlorobenz-aldehyde-ylidene-1-ethylamine-2(2-thiophenyl)imine and an HCN source, in the presence of a non-metallic asymmetric Strecker catalyst to form enantiomerically enriched (S)-α,α-(2-thiophenylethylamino)(2-chlorophenyl)acetonitrile; (b) contacting the enantiomerically enriched (S)-α,α-(2-thiophenylethylamino)(2-chlorophenyl)acetonitrile and a formaldehyde equivalent, in the presence of an acid catalyst to form enantiomerically enriched α-5(4,5,6,7-tetrahydro[3,2-c]thienopyridyl)(2-chlorobenzyl)-nitrile; and (c) contacting the enantiomerically enriched α-5(4,5,6,7-tetrahydro[3,2-c]thienopyridyl)(2-chlorobenzyl)-nitrile and a reagent capable of converting a cyano group into an ester group to form enantiomerically enriched hydrocarbyl ester of (S)-α-(2-chlorophenyl)-6,7-dihydrothieno-[3,2-c]pyridine-5(4H)-acetic acid.

6 Claims, No Drawings

PREPARATION OF (S)-CLOPIDOGREL AND RELATED COMPOUNDS

BACKGROUND OF THE INVENTION

1. Field of the Invention

The present invention relates to a process for enantioselective preparation of (S)-Clopidogrel, a potent platelet aggregation inhibitor, and related compounds. More particularly, the present invention relates to a process for the preparation of (S)-Clopidogrel in high enantioselectivity and yield. (S)-Clopidogrel is used as an antithrombotic agent for treatment of patients with vascular diseases, myocardial infraction and stroke.

2. Description of the Prior Art

Currently there are two known processes for the preparation of (S)-Clopidogrel. Each of these processes relies on classical resolution or enzymatic techniques to introduce the sole chiral center into the molecule.

U.S. Pat. No. 4,847,265 describes a method of preparation of Clopidogrel employing classical resolution techniques.

French Patent Applications Nos. 2,530,247 and 2,769,313 describe commercial methods that are currently used to synthesize Clopidogrel.

When classical resolution techniques are employed, the following problems must be overcome: (1) a suitable resolving agent must be found; (2) the resolving reagent must be recycled to make the resolution economical; and (3) isolation and racemization of the starting material from the mother liquor must be carried out efficiently to improve the economics and overall yield.

The problems with enzymatic resolution techniques are similar to classical resolution techniques in that low yield of the desired enantiomer makes it necessary to isolate and racemize starting material from the mother liquor. An added problem with enzymatic resolution is low volumetric throughput and tedious work up procedures.

To overcome these disadvantages of the prior art, laborious procedures and separations would be required to either enrich the racemic product in one or the other enantiomer or to efficiently and completely separate one enantiomer from the other.

The present invention employs a novel approach, which does not require enzymatic or classical resolution techniques to obtain a final product having high enantioselectivity (ee).

In addition, the present invention overcomes the disadvantages of the prior art described above by providing a process, which enables one to obtain an enantiomerically pure or enantiomerically enriched product without the need for laborious procedures and separations.

SUMMARY OF THE INVENTION

The present invention provides a process for preparing an enantiomerically enriched derivative of (S)-α,α-(2-thiophenylethylamino)(2-chlorophenyl)-acetonitrile intermediate represented by the formula:

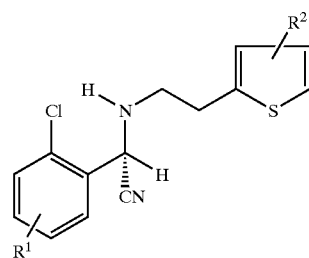

which is an intermediate in the preparation of an enantiomerically enriched derivative of (S)-α-(2-chlorophenyl)-6,7-dihydrothieno[3,2-c]pyridine-5(4H)-acetic acid hydrocarbyl ester represented by the formula:

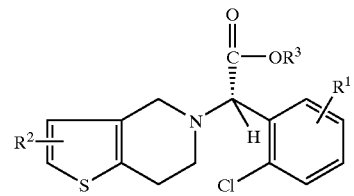

the process including the step of:
contacting a derivative of N-2-chlorobenzaldehydeylidene-1-ethylamine-2(2-thiophenyl)imine represented by the formula:

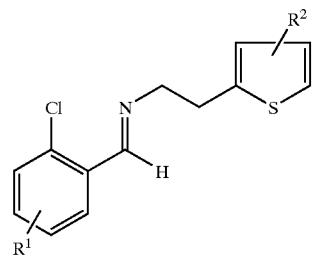

and an HCN source, optionally in the presence of a catalyst represented by the formula:

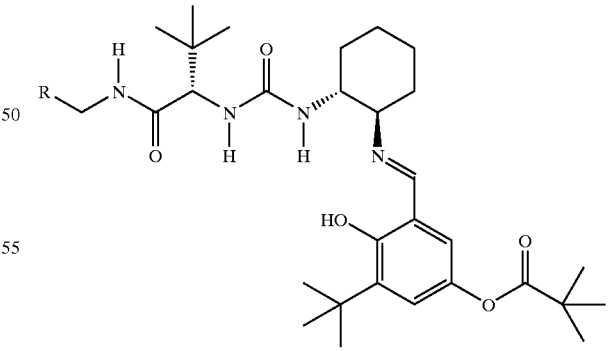

wherin $R^1$ is a substituent at the 3, 4, 5 or 6 position of the chlorophenyl ring and $R^2$ is a substituent at the 4 or 5 position of the thiophene ring;

wherein each $R^1$ and $R^2$ can independently be H, linear, branched or cyclic alkyl of 1 to 22 carbon atoms, aryl of 6 to 22 carbon atoms, aralkyl of 7 to 22 carbon atoms, alkylaryl of 7 to 22 carbon atoms, halogen, cyano, nitro, amido, carbamato, imido, alkoxy, aryloxy, acyl, alkoxycarbonyl and trifluoromethyl;

wherein $R^3$ is a hydrocarbyl group; and wherein R can be phenyl, tolyl, xylyl, naphthyl, heteroaryl, amido, imido, carbamato, polystyrene beads, and a mixture thereof; the contacting being at a temperature and length of time sufficient to form the enantiomerically enriched derivative of (S)-α,α-(2-thiophenylethylamino)(2-chlorophenyl)acetonitrile.

The present invention further provides a process for producing enantiomerically enriched derivative of (S)alpha-(2-chlorophenyl)-6,7-dihydrothieno[3,2-c]pyridine-5 (4H)-acetic acid hydrocarbyl ester, represented by the formula:

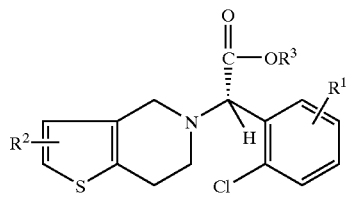

the process including the steps of:

(a) contacting a derivative of N-2-chlorobenzaldeyhydeylidene-1-ethylamine-2 (2-thiophenyl)imine represented by the formula:

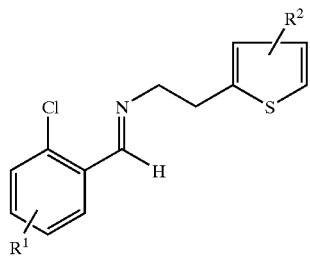

and an HCN source, optionally in the presence of a catalyst represented by the formula:

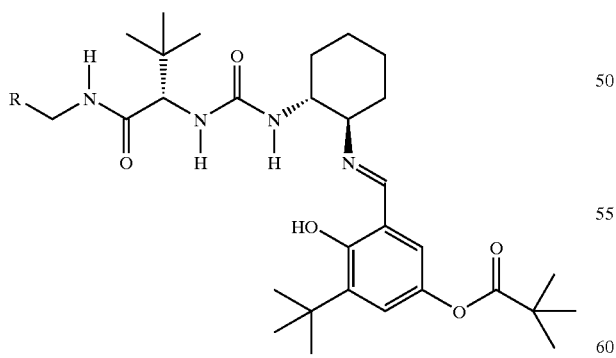

wherein the contacting is carried out at a temperature and length of time sufficient to form a derivative of enantiomerically enriched (S)-α,α-(2-thiophenylethylamino)(2-chlorophenyl)acetonitrile, represented by the formula:

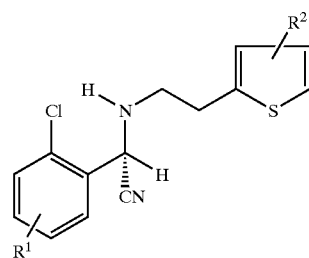

(b) contacting the derivative of enantiomerically enriched (S)-α,α-(2-thiophenylethylamino)(2-chlorophenyl)acetonitrile and a formaldehyde equivalent, optionally in the presence of a catalyst, wherein the contacting is carried out at a temperature and length of time sufficient to form a derivative of enantiomerically enriched α-5 (4,5,6,7-tetrahydro[3,2-c]thienopyridyl)(2-chlorobenzyl)-nitrile, represented by the formula:

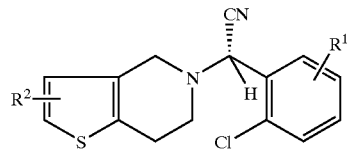

(c) contacting the derivative of enantiomerically enriched α-5(4,5,6,7-tetrahydro[3,2-c]thienopyridyl)(2-chlorobenzyl-nitrile and a reagent capable of converting a cyano group into an ester group at a temperature and length of time sufficient to form a derivative of an enantiomerically enriched hydrocarbyl ester of (S)-α-(2-chlorophenyl)6,7-dihydrothieno-[3,2-c]pyridine-5 (4H)-acetic acid represented by the formula:

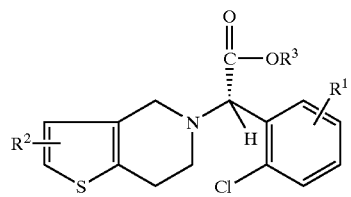

wherin $R^1$ is a substituent at the 3, 4, 5 or 6 position of the chlorophenyl ring and $R^2$ is a substituent at the 4 or 5 position of the thiophene ring; wherein each $R^1$ and $R^2$ can independently be H, linear, branched or cyclic alkyl of 1 to 22 carbon atoms, aryl of 6 to 22 carbon atoms, aralkyl of 7 to 22 carbon atoms, alkylaryl of 7 to 22 carbon atoms, halogen, cyano, nitro, amido, carbamato, imido, alkoxy, aryloxy, acyl, alkoxycarbonyl and trifluoromethyl;

wherein $R^3$ is a hydrocarbyl group; and wherein R can be phenyl, tolyl, xylyl, naphthyl, heteroaryl, amido, imido, carbamato, polystyrene beads, and a mixture thereof.

The present invention still further provides a process for preparing an enantiomerically enriched (S)-α,α-(2-thiophenylethylamino)-(2-chlorophenyl)-acetonitrile represented by the formula:

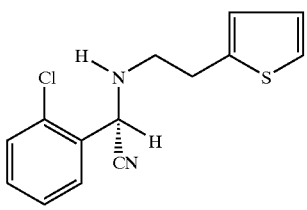

which is an intermediate in the preparation of enantiomerically enriched (S)-α-(2-chlorophenyl)-6,7-dihydrothieno[3,2-c]pyridine-5-(4H)-acetic acid methyl ester represented by the formula:

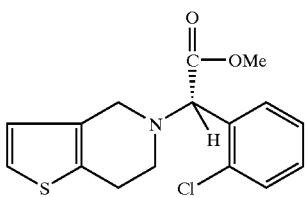

the process including the step of:

contacting N-2-chlorobenzaldehydeylidene-1-ethylamine-2-(2-thiophenyl)-imine represented by the formula:

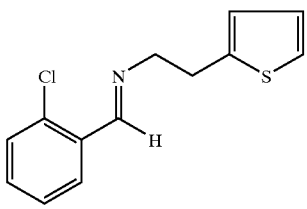

and an HCN source in the presence of a catalyst represented by the formula:

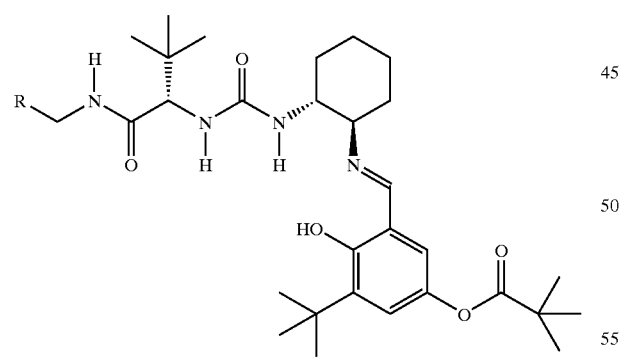

wherein R can be phenyl, tolyl, xylyl, naphthyl, heteroaryl, amido, imido, carbamato, polystyrene beads and a mixture thereof, the contacting being at a temperature and length of time sufficient to form the enantiomerically enriched (S)-α,α-(2-thiophenylethylamino)-(2-chlorophenyl)-acetonitrile.

The present invention also provides process for producing enantiomerically enriched (S)alpha-(2-chlorophenyl)-6,7-dihydro-thieno[3,2-c]pyridine-5 (4H)-acetic acid hydrocarbyl ester, represented by the formula:

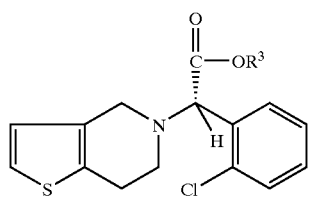

The process includes the steps of:

(a) contacting N-2-chlorobenzaldehydeylidene-1-ethylamine-2(2-thiophenyl)imine represented by the formula:

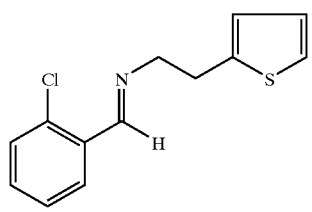

and an HCN source, optionally in the presence of a catalyst represented by the formula:

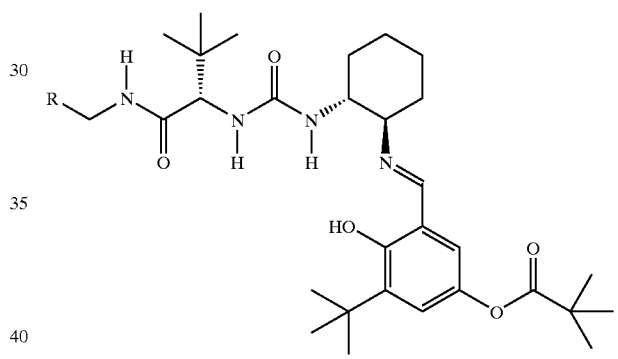

wherein R can be phenyl, tolyl, xylyl, naphthyl, heteroaryl, amido, imido, carbamato, polystyrene beads, and a mixture thereof, wherein the contacting is carried out at a temperature and length of time sufficient to form an enantiomerically enriched (S)-α,α-(2-thiophenylethylamino)(2-chlorophenyl) acetonitrile, represented by the formula:

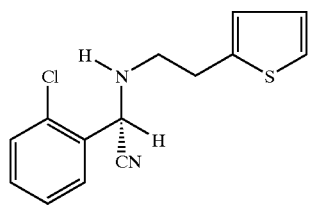

(b) contacting the enantiomerically enriched (S)-α,α-(2-thiophenylethylamino)(2-chlorophenyl)acetonitrile and a formaldehyde equivalent, optionally in the presence of a catalyst, wherein the contacting is carried out at a temperature and length of time sufficient to form enantiomerically enriched α-5(4,5,6,7-tetrahydro[3,2-c]thienopyridyl)(2-chlorobenzyl)-nitrile, represented by the formula:

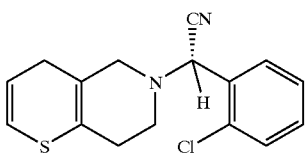

(c) contacting the enantiomerically enriched α-5(4,5,6,7-tetrahydro[3,2-c]thienopyridyl)(2-chlorobenzyl)-nitrile and a reagent capable of converting a cyano group into an ester group at a temperature and length of time sufficient to form an enantiomerically enriched hydrocarbyl ester of (S)-α-(2-chlorophenyl)-6,7-dihydrothieno-[3,2-c]pyridine-5(4H)-acetic acid represented by the formula:

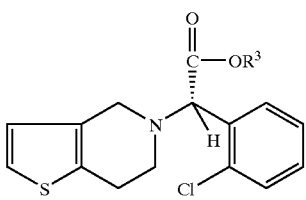

wherein $R^3$ is a hydrocarbyl group.

The advantages of the current process include the production of (S)-Clopidogrel in high ee, high yield and with good volumetric throughput without the need to resort to enzymatic or classical resolution techniques.

DETAILED DESCRIPTION OF THE INVENTION

The present invention provides a process for the preparation of (S)-alpha)-2-chlorophenyl)-6,7-dihydrothieno[3,2-c] pyridine-5 (4H)-acetic acid methyl ester (Clopidogrel) and related compounds.

The process involves the condensation of 2-chlorobenaldehyde with 2-(2-amioethyl)thiophene to yield the corresponding imine. Reaction of the resulting imine with HCN in the presence of a catalyst yields the corresponding cyano amine with enantiomeric excess (hereinafter ee) in the range of 75 to 85% ee.

The present invention does not rely on biocatalysts or classical resolution methods to produce high in the final product. This is achieved by using a catalyst represented by the formula:

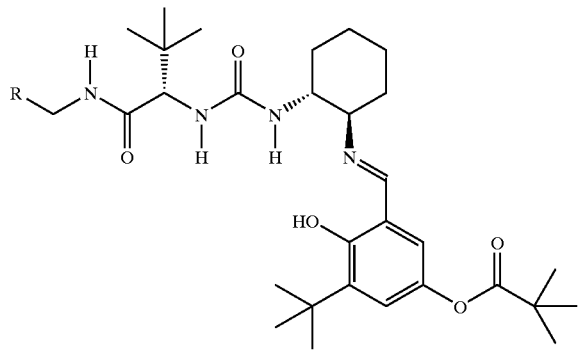

This catalyst can be prepared by a procedure described in a publication by Petr Vachel and Eric N. Jacobsen, *Org. Letters*, Vol 2, No. 6, p.867–870 (2000). This catalyst is sometimes referred to as "Jacobsen non-metallic asymmetric Strecker catalyst."

The resulting amine or its salt, i.e., the HCl salt, may be treated with 1,3 dioxolane to yield the corresponding cyano pyrido thiophene. Then, the Clopidogrel may be isolated by treatment of the cyano pyrido thiophene with acid and an alcohol, such as, methanol.

The present invention provides a process for preparing an enantiomerically enriched derivative of (S)-α,α-(2-thiophenylethylamino)(2-chlorophenyl)-acetonitrile intermediate represented by the formula:

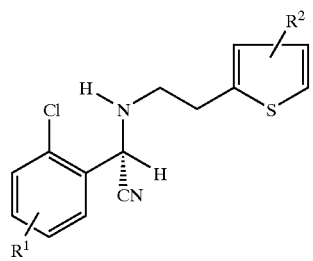

which is an intermediate in the preparation of an enantiomerically enriched derivative of (S)-α-(2-chlorophenyl)-6,7-dihydrothieno[3,2-c]pyridine-5 (4H)-acetic acid hydrocarbyl ester.

The ester is represented by the following formula:

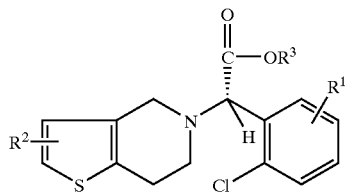

The process includes the step of contacting a derivative of N-2-chlorobenzaldehydeylidene-1-ethylamine-2 (2-thiophenyl)imine represented by the formula:

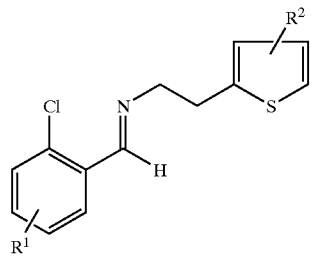

and an HCN source. The contacting step is optionally carried out in the presence of a catalyst represented by the formula:

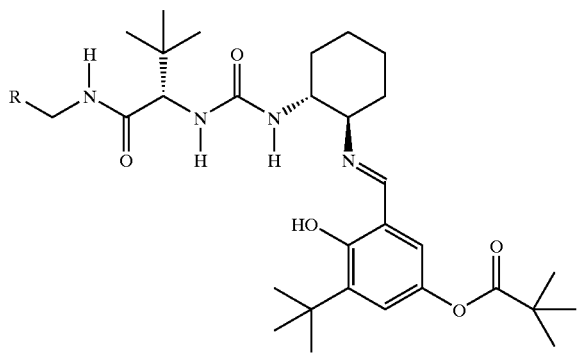

In the compounds described above, R¹ is a substituent at the 3, 4, 5 or 6 position of the chlorophenyl ring and R² is a substituent at the 4 or 5 position of the thiophene ring; each R¹ and R² can independently be H, linear, branched or cyclic alkyl of 1 to 22 carbon atoms, aryl of 6 to 22 carbon atoms, aralkyl of 7 to 22 carbon atoms, alkylaryl of 7 to 22 carbon atoms, halogen, cyano, nitro, amido, carbamato, imido, alkoxy, aryloxy, acyl, alkoxycarbonyl and trifluoromethyl; and R³ is a hydrocarbyl group; and R can be phenyl, tolyl, xylyl, naphthyl, heteroaryl, amido, imido, carbamato, polystyrene beads, and a mixture thereof; the contacting being at a temperature and length of time sufficient to form the enantiomerically enriched derivative of (S)-α,α-(2-thiophenylethylamino)(2-chlorophenyl)acetonitrile.

Preferably, R³ is a linear, branched or cyclic alkyl of 1 to 22 carbon atoms, aryl of 6 to 22 carbon atoms, aralkyl of 7 to 22 carbon atoms, alkylaryl of 7 to 22 carbon atoms or any combination thereof. Compounds wherein R³ is methyl, ethyl or a mixture thereof are preferred.

The derivative of N-2-chlorobenzaldehydeylidene-1-ethylamine-2-(2-thiophenyl)-imine is prepared by a process including the step of contacting an R¹ substituted derivative of 2-chlorobenzaldehyde and an R² substituted derivative of 2-(2-aminoethyl)-thiophene, optionally in the presence of a catalyst, such as, an acid, molecular sieves or a combination thereof, at a temperature and length of time sufficient to produce the derivative of N-2-chlorobenzaldehydeylidene-1-ethylamine-2-(2-thiophenyl)-imine.

The process further includes the step of contacting the enantiomerically enriched derivative of (S)-α,α-(2-thiophenylethyl-amino)-(2-chlorophenyl)-acetonitrile and an acid HX, wherein X is the counter anion of the acid. The contacting step is carried out at a temperature and length of time sufficient to produce a salt of the enantiomerically enriched derivative of (S)-α,α-(2-thiophenyl-ethylamino)-(2-chlorophenyl)-acetonitrile, which is represented by the formula:

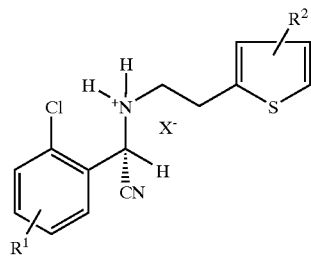

The acid HX can be a mineral acid, an organic acid or a mixture thereof. Examples of such acids include hydrochloric acid, sulfuric acid, phosphoric acid, acetic acid, benzoic acid, trichloroacetic acid, trifluoroacetic acid, trichloromethanesulfonic acid, trifluoromethanesulfonic acid or a mixture thereof. HCl and HOAc are preferred.

The salt of the enantiomerically enriched derivative of (S)-α,α-(2-thiophenylethylamino)-(2-chlorophenyl)-acetonitrile can be purified by recrystallization from a suitable recrystallizing solvent, such as, hexanes, toluene, methanol, ethanol, isopropanol, methylene chloride, tetrahydrofurane, ether, ethyl acetate, acetone or a mixture thereof.

Preferably, the recrystallizing solvent is a mixture including toluene and isopropanol in a 2:1 ratio by weight.

The enantiomerically enriched derivative of (S)-α,α-(2-thiophenylethylamino)(2-chlorophenyl)acetonitrile, or a salt thereof, and a formaldehyde equivalent are then contacted, optionally in the presence of an acid catalyst, such as, hydrochloric acid, sulfuric acid, phosphoric acid, acetic acid, benzoic acid, trichloroacetic acid, trifluoroacetic acid, trichloromethanesulfonic acid, trifluoromethanesulfonic acid or a mixture thereof. The contacting is carried out at a temperature and length of time sufficient to produce enantiomerically enriched α-5-(4,5,6,7-tetrahydro[3,2-c] thienopyridyl)(2-chlorobenzyl)-nitrile, which is represented by the formula:

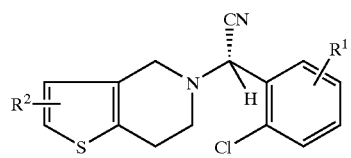

wherein R¹ and R² are as previously described herein above.

The formaldehyde equivalent in the context of the present invention can be formaldehyde, paraformaldehyde, 1,3 dioxolane, formaline, hexamethylenetetraamine or a mixture thereof.

When R¹ and R² are hydrogens, and R³ is methyl, the process of the present invention produces (S)-alpha)-2-chlorophenyl)-6,7-dihydrothieno[3,2-c] pyridine-5 (4H)-acetic acid methyl ester, which is also known as (S)-Clopidogrel.

The various aspects of the present invention are described in the following examples, which are only illustrative and therefore, should not be construed as limiting of the scope of the invention.

EXAMPLE 1

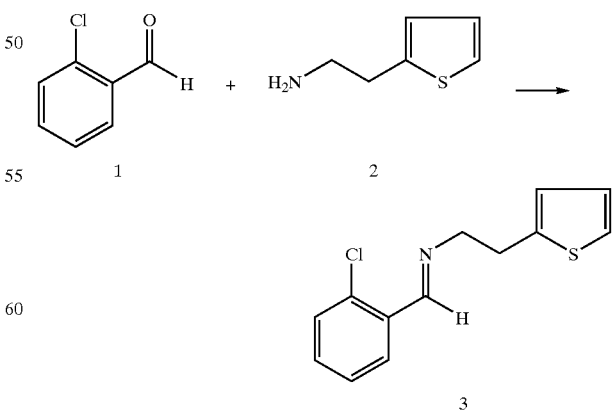

N-2-chlorobenzaldehydeylidene-1-ethylamine-2 (2-thiophenyl)amine (3)

To a solution of hexane (20 mL), at 0° C., was added 4 Å molecular sieves (1 g), 2-chlorobenaldehyde (0.55 g, 0.0048 mmol), and 2(2-aminoethyl)thiophene. The solution was allowed to stir for 1 h, filtered, and evaporated to yield the title compound. The title compound was used in the next step without further purification.

(95% chemical purity) and in 85% ee by evaporation of the reaction solvent, or it may be converted to the corresponding HCl salt 6 by treatment with 1M HCl in acetic acid (2 equiv). The oil is not purified. Recrystallization of HCl salt 6 may be accomplished by heating in a solution of toluene: isopropyl alcohol (2:1 ratio).

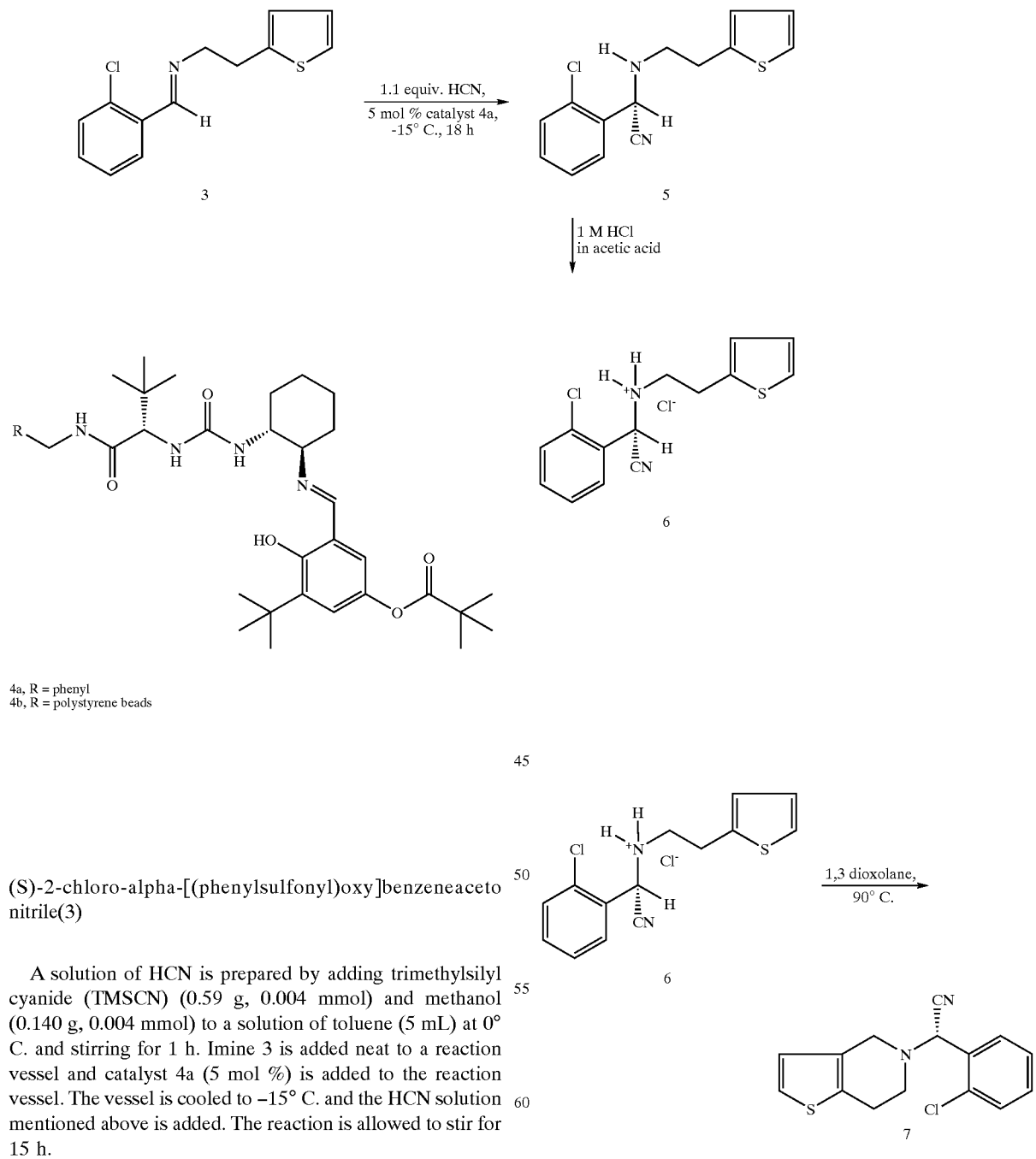

4a, R = phenyl
4b, R = polystyrene beads (S)-2-chloro-alpha-[(phenylsulfonyl)oxy]benzeneacetonitrile(3)

A solution of HCN is prepared by adding trimethylsilyl cyanide (TMSCN) (0.59 g, 0.004 mmol) and methanol (0.140 g, 0.004 mmol) to a solution of toluene (5 mL) at 0° C. and stirring for 1 h. Imine 3 is added neat to a reaction vessel and catalyst 4a (5 mol %) is added to the reaction vessel. The vessel is cooled to −15° C. and the HCN solution mentioned above is added. The reaction is allowed to stir for 15 h.

The completion of the reaction is determined by monitoring the reaction with TLC (10% ethyl acetate in hexane). Amine 5 can be isolated as on oil in near quantitative yield Alpha-5 (4,5,6,7-tetrahydro(3,2-c)thienopyridyl)(2-chlorobenzyl)-nitrile (7)

HCl salt 6 is added to a solution of 1,3-dioxane and heated for 3 h at 90° C. for 8 h. The reaction mixture is allowed to cool and then water (20 mL) is added. The resulting solution is extracted with ethyl acetate (3×20 mL). The organics are dried over sodium sulfate, filtered and evaporated to yield clear oil. The title compound is isolated in near quantitative yield (chemical purity 94%).

(S-alpha)-2-chlorophenyl)-6,7-dihydrothieno[3,2-c]pyridine-5 (4H)-acetic acid methyl ester (Clopidogrel)

Compound 7 can be transformed to the title compound by any method known in the art for the conversion of a nitrile into the corresponding methyl ester.

The process is carried out by condensing 2-chlorobenzaldehyde and 2-aminoethylthipheneto to give the corresponding imine 3. Imine 3 is then treated with a chiral catalyst and HCN at −15° C., i.e., under the asymmetric Strecker conditions.

The chiral catalyst can be either one of the Jacobsen non-metallic Strecker catalyst 1c or 1b, which are described in Petr Vachel and Eric N. Jacobsen, *Org. Letters*, Vol. 2, No. 6, p.867–870 (2000). The Jacobsen non-metallic Strecker catalyst 1c is referred to herein as catalyst 4a. The Jacobsen non-metallic Strecker catalyst 1b is referred to herein as catalyst 4b. The difference between 4a and 4b is that 4a is soluble in organic solvents, while 4b is bound to polystyrene beads. If 4a is used as a catalyst, an 85% ee of the Strecker adduct is obtained. When 4b is used as a catalyst, an ee of 75% is obtained. If the process is practiced in the absence of the Jacobsen non-metallic Strecker catalysts, a further resolution step would be required.

The temperature range for this reaction can be as low as −78° C. and as high as 25° C. The temperature at which the reaction is carried out affects the enantiomeric excess obtained in the final product, with the higher temperatures leading to lower selectivities.

When the asymmetric Strecker reaction is complete, the resulting Strecker adduct 5 is converted to the corresponding HCl salt 6. The salt of Strecker adduct 5 may be formed by treatment with any inorganic acid, i.e., HBr, hydrogen sulfate, and taurochlorate. HCl salt 6 may be enantiomerically upgraded by recrystallization from a 2:1 toluene: Isopropyl alcohol solution or be carried onto the next step. The HCl salt 6 is converted to cyano thiophene 7. This is accomplished by any of the well-known methods for Pictet-Spengler type reactions (for leading references see: Ohno et al, *Chem. Pharm. Bull.*, 1994, 42, 1676–1678).

Compound 5 or 6 can be treated with acid and formaldehyde or formaldehyde equivalent to give the compound 7. Compound 7 can then be converted to Clopidogrel by treatment with methanol in the presence of any suitable acid known in the art. Similarly, compound 7 can be hydrolyzed to the corresponding carboxylic acid by reagents known for this transformation and then treated with any reagent known to convert carboxylic acids to methyl ester.

(S)-alpha)-2-chlorophenyl)-6,7-dihydrothieno[3,2-c]pyridine-5 (4H)-acetic acid methyl ester, known as (S)-Clopidogrel, has utility as a platelet aggregation inhibitor and is described as being an antithrombotic agent in patients with vascular diseases, myocardial infraction and stroke.

The present invention has been described with particular reference to the preferred embodiments. It should be understood that variations and modifications thereof can be devised by those skilled in the art without departing from the spirit and scope of the present invention. Accordingly, the present invention embraces all such alternatives, modifications and variations that fall within the scope of the appended claims.

What is claimed is:

1. A process for producing enantiomerically enriched derivative of (S)-α-(2-chlorophenyl)-6,7-dihydrothieno[3,2-c]pyridine-5 (4H)-acetic acid hydrocarbyl ester, represented by the formula:

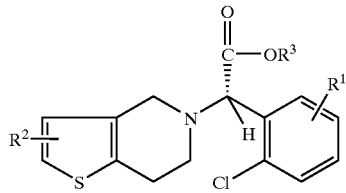

said process comprising the steps of:

(a) contacting a derivative of N-2-chlorobenzaldehydeylidene-1-ethylamine-2 (2-thiophenyl)imine represented by the formula:

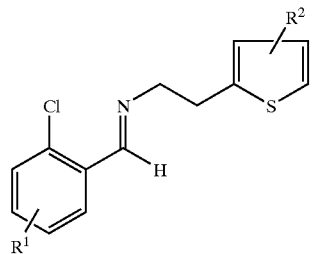

and an HCN source, optionally in the presence of a catalyst represented by the formula:

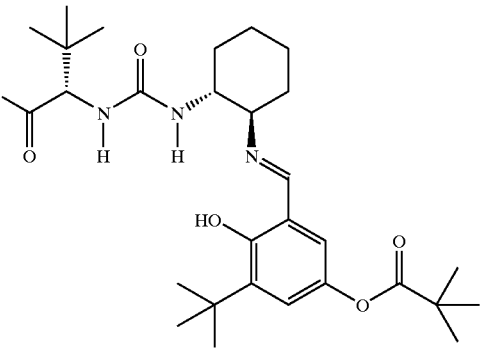

wherein said contacting is carried out at a temperature and length of time sufficient to form a derivative of enantiomerically enriched (S)-α,α-(2-thiophenylethylamino)(2-chlorophenyl)acetonitrile, represented by the formula:

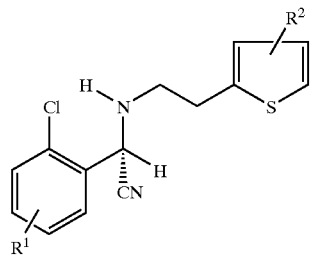

(b) contacting said derivative of enantiomerically enriched (S)-α,α-(2-thiophenylethylamino)(2-chlorophenyl)acetonitrile and a formaldehyde equivalent, optionally in the presence of a catalyst, wherein said contacting is carried out at a temperature and length of time sufficient to form a derivative of enantiomerically enriched α-5(4,5,6,7-tetrahydro[3,2-c]thienopyridyl)(2-chlorobenzyl)-nitrile, represented by the formula:

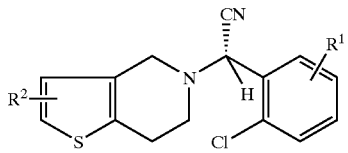

and (c) contacting said derivative of enantiomerically enriched α-5(4,5,6,7-tetrahydro[3,2-c]thienopyridyl)(2-chlorobenzyl)-nitrile and a reagent capable of converting a cyano group into an ester group at a temperature and length of time sufficient to form a derivative of an enantiomerically enriched hydrocarbyl ester of (S)-α-(2-chlorophenyl)-6,7-dihydrothieno-[3,2-c]pyridine-5(4H)-acetic acid represented by the formula:

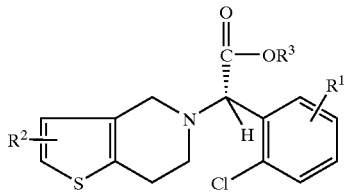

wherein $R^1$ is a substituent at the 3, 4, 5 or 6 position of the chlorophenyl ring and $R^2$ is a substituent at the 4 or 5 position of the thiophene ring; wherein each $R^1$ and $R^2$ is independently selected from the group consisting of: H, linear, branched or cyclic alkyl of 1 to 22 carbon atoms, aryl of 6 to 22 carbon atoms, aralkyl of 7 to 22 carbon atoms, alkylaryl of 7 to 22 carbon atoms, halogen, cyano, nitro, amido, carbamato, imido, alkoxy, aryloxy, acyl, alkoxycarbonyl and trifluoromethyl;

wherein $R^3$ is a hydrocarbyl group; and wherein R is selected from the group consisting of: phenyl, tolyl, xylyl, naphthyl, heteroaryl, amido, imido, carbamato, polystyrene beads, and a mixture thereof.

2. The process of claim 1, wherein $R^3$ is selected from the group consisting of: a linear, branched or cyclic alkyl of 1 to 22 carbon atoms, aryl of 6 to 22 carbon atoms, aralkyl of 7 to 22 carbon atoms, alkylaryl of 7 to 22 carbon atoms and any combination thereof.

3. The process of claim 2, wherein $R^3$ is selected from the group consisting of: methyl, ethyl and a mixture thereof.

4. A process for producing enantiomerically enriched (S)-α-(2-chlorophenyl)-6,7-dihydrothieno[3,2-c]pyridine-5(4H)-acetic acid hydrocarbyl ester, represented by the formula:

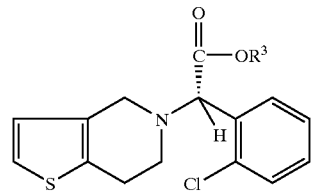

said process comprising the steps of:

(a) contacting N-2-chlorobenzaldehydeylidene-1-ethylamine-2 (2-thiophenyl)imine represented by the formula:

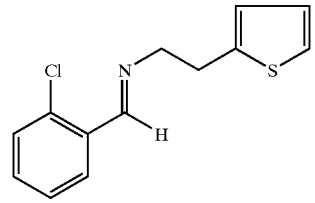

and an HCN source, optionally in the presence of a catalyst represented by the formula:

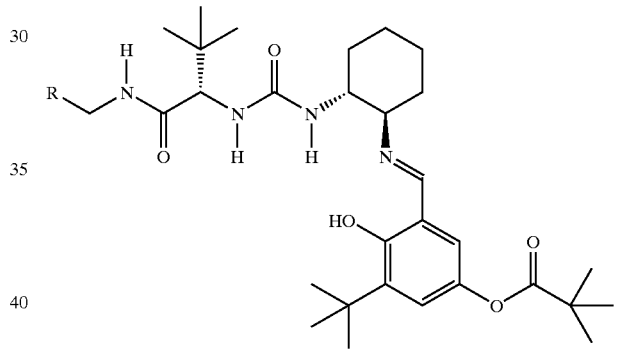

wherein R is selected from the group consisting of: phenyl, tolyl, xylyl, naphthyl, heteroaryl, amido, imido, carbamato, polystyrene beads, and a mixture thereof, wherein said contacting is carried out at a temperature and length of time sufficient to form an enantiomerically enriched (S)-α,α-(2-thiophenylethylamino)(2-chlorophenyl)acetonitrile, represented by the formula:

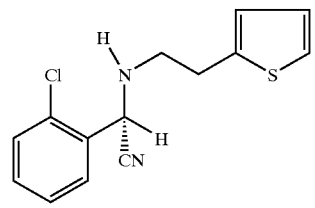

(b) contacting said enantiomerically enriched (S)-α,α-(2-thiophenylethylamino)(2-chlorophenyl)acetonitrile and a formaldehyde equivalent, optionally in the presence of a catalyst, wherein said contacting is carried out at a temperature and length of time sufficient to form enantiomerically enriched α-5(4,5,6,7-tetrahydro[3,2- c]thienopyridyl)(2-chlorobenzyl)-nitrile, represented by the formula:

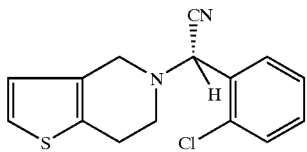

and (c) contacting said enantiomerically enriched α-5(4,5,6,7-tetrahydro[3,2-c]thienopyridyl)(2-chlorobenzyl)-nitrile and a reagent capable of converting a cyano group into an ester group at a temperature and length of time sufficient to form an enantiomerically enriched hydrocarbyl ester of (S)-α-(2-chlorophenyl)-6,7-dihydrothieno-[3,2-c]pyridine-5(4H)-acetic acid represented by the formula:

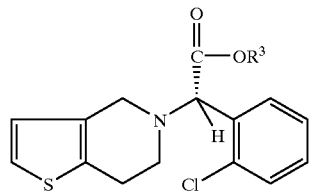

wherein $R^3$ is a hydrocarbyl group.

5. The process of claim 4, wherein $R^3$ is selected from the group consisting of: a linear, branched or cyclic alkyl of 1 to 22 carbon atoms, aryl of 6 to 22 carbon atoms, aralkyl of 7 to 22 carbon atoms, alkylaryl of 7 to 22 carbon atoms and any combination thereof.

6. The process of claim 5, wherein $R^3$ is selected from the group consisting of: methyl, ethyl and a mixture thereof.

\* \* \* \* \*